(12) United States Patent
Cho et al.

(10) Patent No.: US 8,777,850 B2
(45) Date of Patent: Jul. 15, 2014

(54) HEART FAILURE PATIENT MANAGEMENT USING AN IMPLANTABLE MONITORING SYSTEM

(75) Inventors: Yong K. Cho, Maple Grove, MN (US); Ven R. Manda, Stillwater, MN (US); Brandon S. Sparks, Shoreview, MN (US); Tommy D. Bennett, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 914 days.

(21) Appl. No.: 12/262,254

(22) Filed: Oct. 31, 2008

(65) Prior Publication Data

US 2010/0113890 A1 May 6, 2010

(51) Int. Cl.
*A61B 5/00* (2006.01)

(52) U.S. Cl.
USPC ........... 600/300; 128/905; 128/920; 128/923; 600/301; 600/481; 600/482; 600/483; 600/484; 600/485; 600/486; 600/487

(58) Field of Classification Search
USPC .................. 128/905, 920, 923; 600/300, 301, 600/481–487
See application file for complete search history.

(56) References Cited

U.S. PATENT DOCUMENTS

| | | | |
|---|---|---|---|
| 5,368,040 A | 11/1994 | Carney | |
| 5,535,752 A | 7/1996 | Halperin | |
| 5,564,434 A | 10/1996 | Halperin | |
| 6,155,267 A * | 12/2000 | Nelson | 128/899 |
| 6,438,408 B1 | 8/2002 | Mulligan | |
| 6,580,946 B2 | 6/2003 | Struble | |
| 6,599,250 B2 | 7/2003 | Webb | |
| 6,865,419 B2 | 3/2005 | Mulligan | |
| 7,367,951 B2 | 5/2008 | Bennett | |
| 2004/0147969 A1 | 7/2004 | Mann et al. | |
| 2005/0027323 A1 | 2/2005 | Mulligan et al. | |
| 2006/0020295 A1 | 1/2006 | Brockway et al. | |
| 2006/0074404 A1 * | 4/2006 | Struble | 604/890.1 |
| 2006/0167359 A1 * | 7/2006 | Bennett et al. | 600/485 |
| 2007/0255112 A1 | 11/2007 | Taepke et al. | |
| 2007/0255327 A1 | 11/2007 | Cho et al. | |
| 2008/0091114 A1 | 4/2008 | Min et al. | |
| 2008/0157980 A1 | 7/2008 | Sachanandani et al. | |
| 2008/0162182 A1 | 7/2008 | Cazares et al. | |
| 2008/0275349 A1 * | 11/2008 | Halperin et al. | 600/484 |
| 2011/0061647 A1 * | 3/2011 | Stahmann et al. | 128/202.16 |

FOREIGN PATENT DOCUMENTS

| | | |
|---|---|---|
| EP | 706808 B1 * | 5/2002 |
| WO | 03/037428 A2 | 5/2003 |
| WO | 2006/081432 A1 | 8/2006 |
| WO | 2006081453 | 8/2006 |
| WO | 2007079337 | 7/2007 |
| WO | 2008/014078 A2 | 1/2008 |

OTHER PUBLICATIONS (PCT/US2009/060316) PCT Notification of Transmittal of the International Search Report and the Written Opinion of the International Searching Authority, Mailed Jun. 9, 2011, 18 pages.

* cited by examiner

*Primary Examiner* — Melanie Y Brown
*Assistant Examiner* — Erik B Crawford
(74) *Attorney, Agent, or Firm* — Michael C. Soldner

(57) ABSTRACT

An implantable medical device system and method provide physiological variable monitoring for use in patient management. A target value for a physiological variable and formulations for computing metrics of the physiological variable are stored. Values of the physiological variable are determined from a sensed physiological signal and are used to compute a selected metric. The metric is compared to the stored target value.

29 Claims, 5 Drawing Sheets

HEART FAILURE PATIENT MANAGEMENT USING AN IMPLANTABLE MONITORING SYSTEM

TECHNICAL FIELD

The disclosure relates generally to implantable medical devices and, in particular, to an implantable medical device for monitoring a patient and providing information for clinically managing the patient.

BACKGROUND

Physicians caring for heart failure patients face many challenges in selecting optimal medical regimens. Heart failure mechanisms are complex and many hemodynamic and autonomic variables can be affecting the overall heart performance. Monitoring heart failure in a clinical setting can be expensive, time-consuming, and invasive, thereby posing risk and discomfort to the patient, while still yielding measurements of hemodynamic variables or other clinical indicators of heart failure only at particular points in time. An implantable hemodynamic monitor (IHM), such as the Chronicle®, Medtronic, Inc., Minneapolis, Minn., can provide ambulatory monitoring of heart failure, including monitoring of blood pressure, heart rate, patient activity, and thoracic fluid status. Clinicians previously accustomed to having limited measurements, perhaps only non-invasive or subjective measurements taken at specific time points, now have extensive data available to them relating to multiple objective heart failure variables acquired continuously or at periodic intervals, over days, weeks, months, or even years. This extensive data presents a new challenge in how to efficiently and effectively evaluate and apply the data in managing an individual heart failure patient. Methods for managing heart failure patients utilizing the data provided by an IHM are needed.

DETAILED DESCRIPTION

Figure 1:
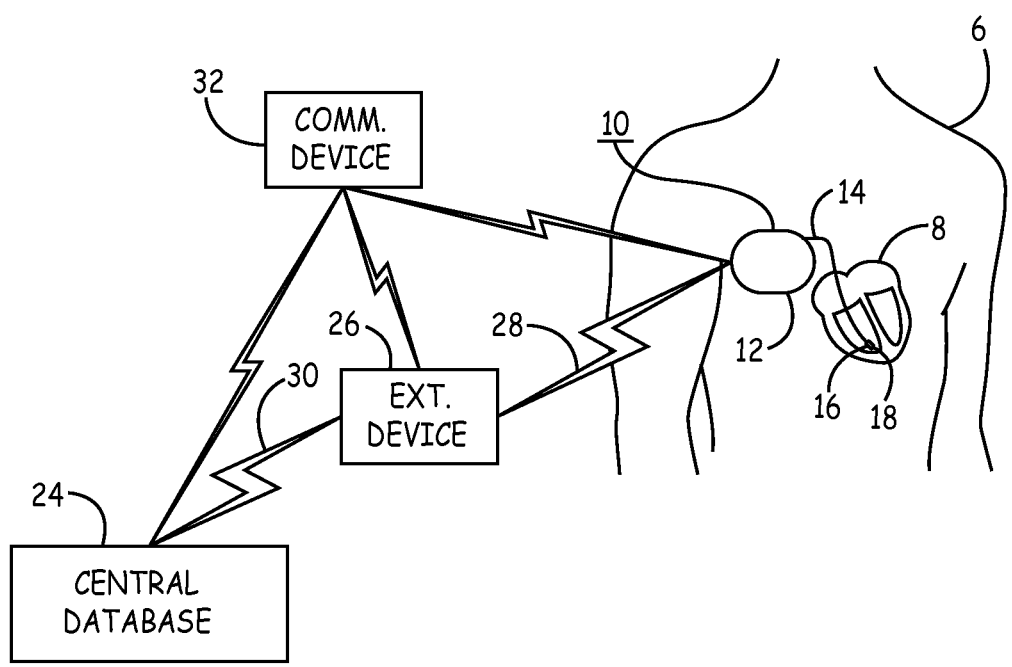
FIG. 1 is a schematic diagram of an implantable medical device (IMD) coupled to a lead positioned within a heart in a patient's body.

In the following description, references are made to illustrative embodiments. It is understood that other embodiments may be utilized without departing from the scope of the invention. For purposes of clarity, the same reference numbers are used in the drawings to identify similar elements. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

Methods and associated apparatus described herein generally relate to managing heart failure patients though it is recognized that the methods described may be utilized for other patient management applications. The term "heart failure variable" as used herein refers to any variable derived from a physiological signal useful in monitoring heart failure status. A heart failure variable may be determined from a variety of physiological signals and is any variable that changes with a progression of heart failure. A heart failure variable is a variable derived from a raw signal for example over one heart beat or a group of heart beats, such as a systolic pressure, a diastolic pressure, a mean pressure, etc. In other applications, any physiological variable useful in monitoring a patient condition may be measured.

As will be described herein, metrics of the physiological or heart failure variable are computed using multiple measured values of the variable. Heart failure variable metrics are generally defined as a statistical aspect of a measured heart failure variable, such as a mean or median of a number of heart failure variable values measured over a period of time. In some embodiments, the heart failure variable may be thought of as an "instantaneous" measurement in that it may be measured at one point in time or during one cardiac cycle. Examples of such instantaneous measurements include a systolic pressure, a diastolic pressure, a stroke volume, or a heart rate. A metric of a heart failure variable may then be considered as a statistical measure of multiple instantaneous measurements acquired over a period of time, such as an hourly, daily or weekly average of the instantaneously measured variable.

FIG. 1 is a schematic diagram of an implantable medical device (IMD) 10 coupled to a lead 14 positioned within a heart 8 in a patient's body 6. IMD 10 is capable of monitoring at least one physiological signal from which variables useful in monitoring heart failure can be measured or derived. IMD 10 may or may not be provided with therapy delivery capabilities. IMD 10 may correspond to a variety of implantable medical devices including a cardiac pacemaker, implantable cardioverter defibrillator, implantable hemodynamic monitor, a drug pump, a neurostimulator or the like. Accordingly, IMD 10 may be coupled to additional leads and/or catheters operatively positioned relative to the patient's heart 8 or other body tissues for deploying stimulating/sensing electrodes, other physiological sensors, and/or drug delivery ports. While lead 14 is shown terminated within the right ventricle of the patient's heart, it is recognized that lead 14 may be configured as a transvenous lead that extends into other heart chambers or blood vessels for positioning electrodes and/or physiological sensors in a desired location.

Housing 12 encloses circuitry (not shown in FIG. 1) included in IMD 10 for controlling and performing device functions and processing sensed signals. In one embodiment, IMD 10 corresponds to an implantable hemodynamic monitor capable of sensing and recording cardiac electrogram (EGM) signals, intracardiac right ventricular pressure signals, patient activity signals, core body temperature signals, and transthoracic impedance signals. IMD 10 may store sensed signals and derives heart failure variable values from the sensed signals for monitoring heart failure.

EGM signals are sensed using one or more electrodes 18 carried by lead 14 and optionally housing 12 of IMD 10. An electrode 18 carried by lead 14 is also used with IMD housing 12 for measuring a transthoracic impedance for use in monitoring intrathoracic fluid status. As used herein, "transthoracic" impedance refers to any impedance measurement across a portion of the thorax, including across a portion of the heart, lungs and/or pulmonary vascular bed. In alternative embodiments, one or more lead-based electrodes and/or one or more subcutaneously placed electrodes, incorporated on IMD housing 12 or carried by a subcutaneously extending lead, may be used to measure transthoracic impedance across a portion of the thoracic cavity, heart or lungs for use in deriving a variable useful in monitoring heart failure status. Intracardiac impedances may also be used in determining a heart failure variable for monitoring a heart condition. For the purposes of the discussion herein, intracardiac impedance can be considered as one type of transthoracic impedance measurement in that intracardiac impedance is measured using electrodes within or on the heart to measure impedance across the heart or any portion of the heart.

Transthoracic impedance decreases with heart failure decompensation as fluid accumulates in the chest and the heart dilates due to elevated right and/or left heart filling pressures and insufficient cardiac ejection. Electrical impedance decreases as the fluid in the chest increases. As such, transthoracic impedance measurements may be used in deriving a heart failure variable useful in monitoring heart failure.

Lead 14 is further provided with a pressure sensor 16. Pressure sensor 16 is used for monitoring pressure within the right ventricle (RV) for use in deriving values of a heart failure variable. The RV pressure signal can be used to measure instantaneous values of a peak systolic pressure, peak diastolic pressure or an estimated pulmonary artery diastolic pressure (ePAD). Pulmonary artery pressure increases with a worsening of congestive heart failure and thus ePAD is a useful heart failure variable in patient management. It is recognized that numerous other pressure-related variables derived from the RV pressure signal can be useful in monitoring heart failure. Furthermore, pressure signals obtained at other locations in the heart or vasculature, such as in the pulmonary artery, may be used for deriving or measuring a heart failure variable. Derivation of various pressure-related variables that may be used in monitoring a cardiac condition is generally described in U.S. Pat. No. 6,865,419 (Mulligan) and U.S. Pat. No. 7,367,951 (Bennett), both patents incorporated herein by reference in their entirety.

IMD 10 is capable of bidirectional communication with an external device 26 via telemetry link 28. Device 26 may be embodied as a programmer or home monitor used to program the operating mode and various operational parameters of IMD 10 and/or interrogate IMD 10 to retrieve data stored by IMD 10. Stored data may include data related to IMD function determined through automated self-diagnostic tests as well as physiological data acquired by IMD 10. Device 26 may be provided with external monitoring capabilities such as blood pressure monitoring. As such device 26 may provide a reference pressure for calibration of pressure measurements obtained using implanted pressure sensor 16 and for adjusting for ambient pressure. External device 26 may be configured to receive user-input relating to additional patient data, such as body weight, medication schedules, physical symptoms, or other subjective or objective externally monitored data. Such data may be received by device 26 by direct connections or user interface or by wireless communications methods such as infra-red, radio frequency signals or the like.

External device 26 is further shown in communication with a central database 24 via communication link 30, which may be a wireless or hardwired link. Programming and interrogation data may be transmitted via link 30. Central database 24 may be a centralized computer, web-based or other networked database used by a clinician for remote monitoring and management of patient 6. Central database 24 is also referred to herein as "remote patient management database".

Communication device 32 may be a cellular phone or other handheld device enabled for wireless communication with IMD 10, external device 26, and/or central database 24 to receive patient and/or clinician notifications from IMD 10, external device 26 or central database 24 regarding the status of a monitored heart failure variable. Communication devices and networks for use with implantable device systems are generally disclosed, for example, in U.S. Pat. No. 6,418,346 (Nelson, et al.), incorporated herein by reference in its entirety. Communication device 32 may represent a device used by a clinician to send and receive data regarding patient 6 or a device used by patient 6 to send and receive data. For example, a clinician using central database 24 may receive data from IMD 10 via external device 26 then provide a patient with instructions by sending information from central database 24 to communication device 32.

While not explicitly shown in FIG. 1, it is recognized that each of external device 26, database 24 and communication device 32 include some type of user-interface to allow a patient or clinician to enter data or information into the respective device. Such interfaces may include a key board, mouse, microphone for receiving voiced commands, touch screen, graphical user interface or the like. Entered data may include programming commands, interrogation commands, patient symptoms, externally monitored physiological data, and data relating to therapy interventions.

Various methods described herein and executed for monitoring heart failure of a patient using one or more physiological signals sensed by IMD 10 may be implemented in one component of the IMD system shown in FIG. 1 or distributed across IMD system components, namely IMD 10, external device 26, communication device 32, and/or central database 24. The implementation may include any combination of hardware, firmware and/or software.

Figure 2:
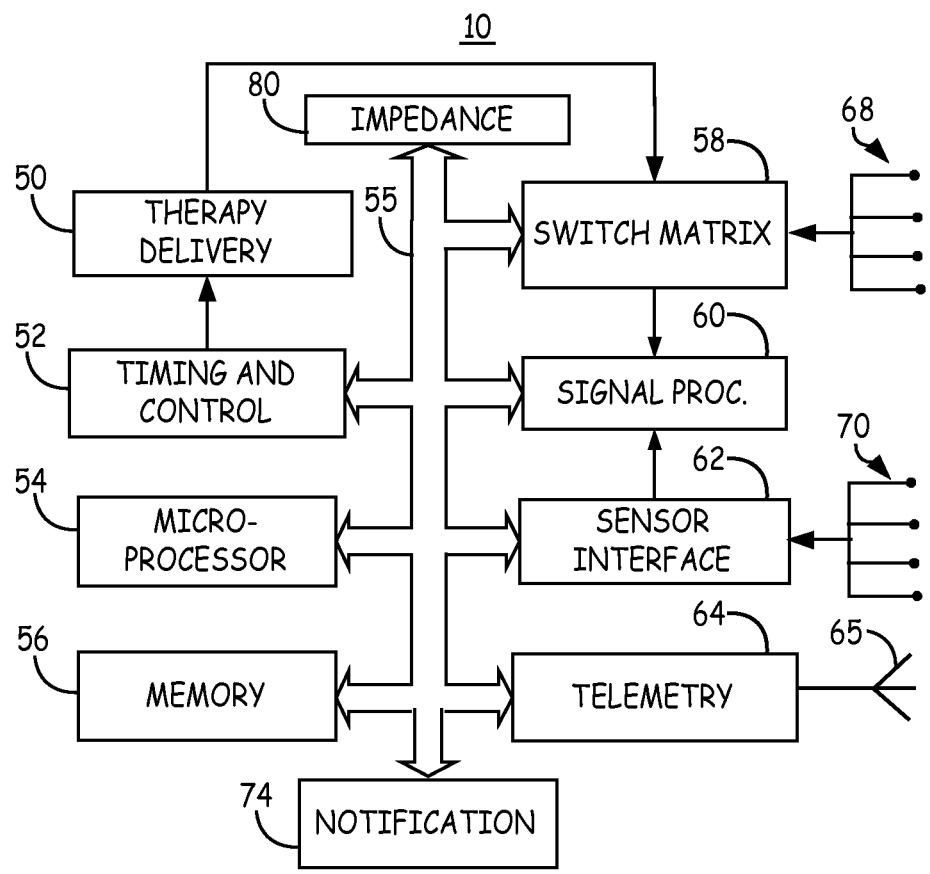
FIG. 2 is a functional block diagram of one embodiment of an IMD.

FIG. 2 is a functional block diagram of one embodiment of IMD 10. IMD 10 generally includes timing and control circuitry 52 and a control unit that may employ microprocessor 54 or a digital state machine for timing sensing and therapy delivery functions (when present) in accordance with a programmed operating mode. Microprocessor 54 and associated memory 56 are coupled to the various components of IMD 10 via a data/address bus 55.

IMD 10 may include therapy delivery module 50 for delivering a therapy in response to determining a need for therapy, e.g., based on sensed physiological signals. Therapy delivery module 50 may provide drug delivery therapies or electrical stimulation therapies, such as cardiac resynchronization therapy, cardiac pacing or anti-arrhythmia therapies. Therapies are delivered by module 50 under the control of timing and control circuitry 52.

If IMD 10 is provided with therapy delivery capabilities, therapy delivery module 50 is coupled to two or more electrode terminals 68 via an optional switch matrix 58. Switch matrix 58 may be used for selecting which electrodes and corresponding polarities are used for delivering electrical stimulation pulses. Terminals 68 may be coupled to connectors providing electrical connection to electrodes incorporated in IMD housing 12 or other lead-based electrodes, including electrode(s) 18 carried by lead 14 (shown in FIG. 1).

Electrode terminals 68 are also used for receiving cardiac EGM signals through any unipolar or bipolar sensing configuration. EGM signals may be monitored for use in diagnosing or managing a patient condition or may be used for determining when a therapy is needed and controlling the timing and delivery of the therapy. When used for sensing, electrode terminals 68 are coupled to signal processing circuitry 60 via switch matrix 58. Signal processor 60 includes sense amplifiers and may include other signal conditioning circuitry and an analog-to-digital converter. EGM signals may then be used by microprocessor 54 for detecting physiological events, such as detecting and discriminating cardiac arrhythmias. EGM signals may be used for determining a heart rate for use in computing metrics of measured heart failure variables.

As discussed above, IMD 10 may measure impedance signals for deriving a thoracic fluid status. As such, electrode terminals 68 are used for coupling selected electrodes to impedance measuring module 80 for providing an impedance measurement drive signal along an excitation path. The voltage is then measured across selected measuring electrodes allowing the impedance across the measurement path to be computed from the known drive signal and the measured voltage. Impedance measurement methods and associated apparatus are generally disclosed in PCT Publication WO 2008/014078 (Stylos), incorporated herein by reference in its entirety.

IMD 10 is additionally coupled to one or more sensors of physiological signals via sensor terminals 70. Physiological sensors include a pressure sensor 16 as shown in FIG. 1 and may further include accelerometers, flow sensors, blood chemistry sensors, activity sensors, postures sensors, or other physiological sensors used in conjunction with implantable medical devices. Physiological sensors may be carried by leads extending from IMD 10 or incorporated in or on the IMD housing 12.

Signals received at sensor terminals 70 are received by a sensor interface 62 which provides sensor signals to signal processing circuitry 60. Sensor interface 62 receives the sensor signal and may provide initial amplification, filtering, rectification, or other signal conditioning. Sensor signals are used by signal processor 60 and/or microprocessor 54 for detecting physiological events or conditions. Sensed signals are used for deriving or measuring values of heart failure variables. In some embodiments, a primary sensor is used to measure instantaneous values of a heart failure variable. A secondary sensor, which senses a signal corresponding to a secondary effect on the heart failure variable, is used to acquire data for computing metrics of the heart failure variable. In one embodiment, signals from pressure sensor 16 are processed by signal processor 60 and/or microprocessor 54 for measuring a value of a pressure variable used for computing a metric of the pressure variable. A secondary sensor, for example an activity sensor, is used to enable computation of the pressure variable metric at different activity levels. Other secondary sensors may include activity, posture, respiration, temperature or heart rate sensors.

Formulations for computing metrics of a heart failure variable may be stored in memory 56 and used by microprocessor 54 with input received from electrode terminals 68, sensor terminals 70, processor 60 and impedance measuring module 80. As will be described herein, microprocessor 54 in conjunction with memory 56 operates as a control unit for executing software-implemented algorithms for computing metrics of heart failure variables derived from sensed signals by processor 60, impedance module 80, and/or by microprocessor 54.

One or more metrics for a given heart failure variable is then compared to a target value stored in memory 56. The target value, as will be described in greater detail, is a clinically significant value of the heart failure variable. Heart failure monitoring algorithms may be stored in memory 56 and retrieved therefrom by microprocessor 54 as needed. In alternative embodiments, functionality described herein may be implemented using dedicated hardware and/or firmware.

Memory 56 may store a variety of programmed-in operating modes and parameter values that are used by microprocessor 54. The memory 56 may also be used for storing data compiled from sensed physiological signals and/or relating to device operating history for telemetry out on receipt of a retrieval or interrogation instruction. Microprocessor 54 may respond to the data by altering a therapy, triggering data storage, and/or enabling other sensors for acquiring physiological data. Notification module 74 generates a notification message for the patient and/or a clinician in response to comparisons between stored target values and comparison metrics computed from measured heart failure variables. Notifications may be transmitted to an external device using telemetry module 64. In some embodiments, notification module may generate an alert signal perceivable by the patient, such as an acoustical signal or vibration.

IMD 10 further includes telemetry module 64 and antenna 65. Programming commands or data are transmitted during uplink or downlink via wireless telemetry between IMD telemetry module 64 and external telemetry circuitry included in an external device.

Figure 3:
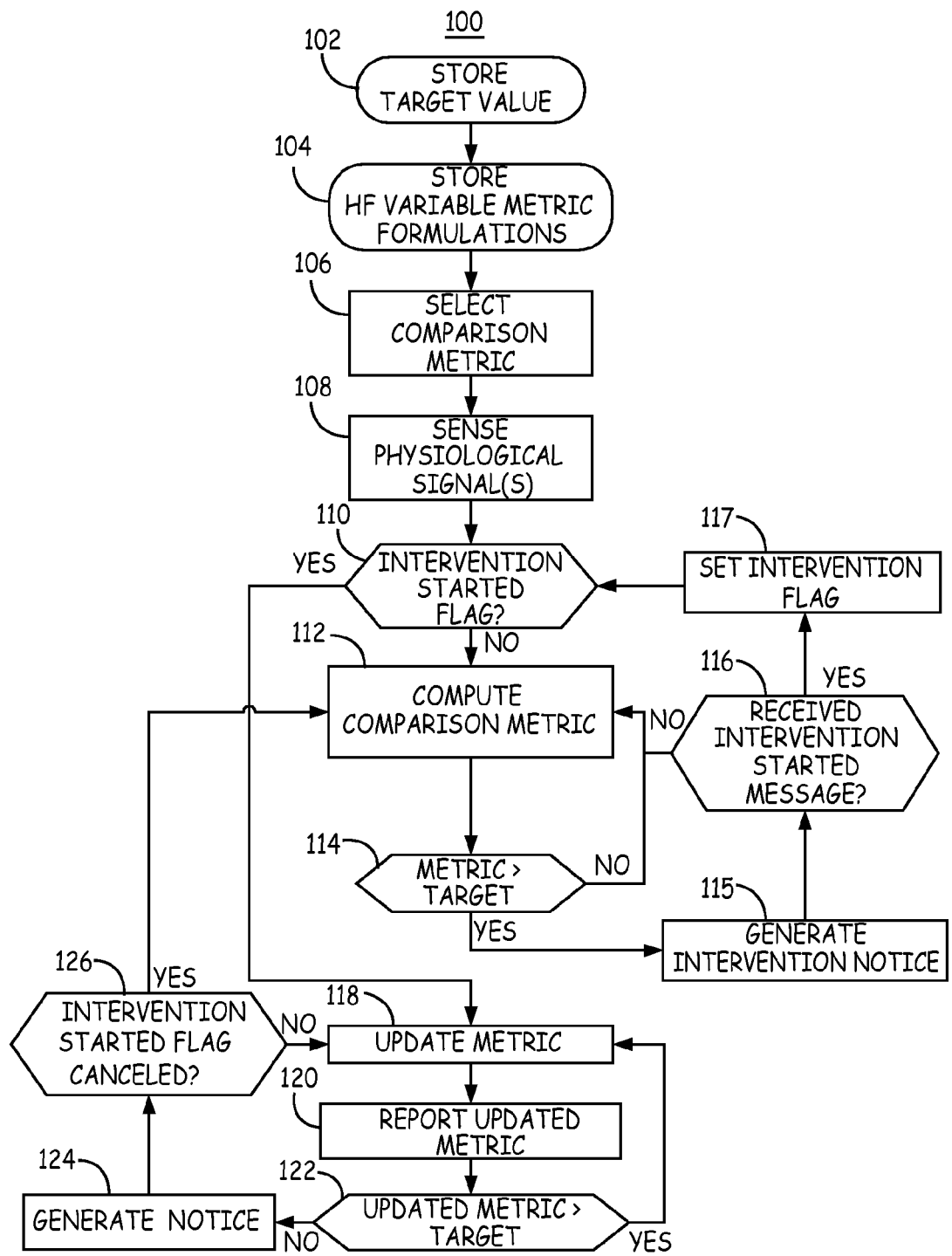
FIG. 3 is a flow chart of one embodiment of a method for managing a patient using a target value and comparison metrics of a heart failure variable derived from IMD sensed physiological signals.

FIG. 3 is a flow chart of one embodiment of a method 100 for managing a patient using a predetermined target value and metrics of a heart failure variable derived from IMD sensed physiological signals. Flow chart 100 is intended to illustrate the functional operation of the device, and should not be construed as reflective of a specific form of software or hardware necessary to implement the methods described. It is believed that the particular form of software will be determined primarily by the particular system architecture employed in the device and by the particular sensing and therapy delivery methodologies employed by the device. Providing software to accomplish the functionality described herein in the context of any modern IMD, given the disclosure herein, is within the abilities of one of skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

Method 100 includes storing a target value for a heart failure variable at block 102. The target value is a clinically relevant value for a heart failure variable that is used in managing the patient's heart failure condition. The target value is a value which when exceeded by the heart failure variable indicates a clinically relevant worsening or instability of heart failure and below which indicates the heart failure is stabilized. The target value is generally selected as value that is meaningful to a clinician regardless of whether the value is being applied to an instantaneous measurement of a heart failure variable or any statistical metric of the heart failure variable. As such, a single target value is stored for a given heart failure variable, regardless of what metrics will be computed for the given heart failure variable.

In one embodiment, the heart failure variable of interest is ePAD. Generally, ePAD is determined as the RV pressure occurring at an inflection point in the RV pressure waveform which corresponds to the time of pulmonary valve opening. The time of this inflection point can be found by identifying the time of the peak of the first time derivative of the RV pressure signal. Methods for deriving ePAD are generally described in U.S. Pat. No. 5,368,040 (Carney), incorporated herein by reference in its entirety. An ePAD target value may be selected based on clinical data from a patient population or selected based on a patient's individual condition. In one embodiment, a target value for ePAD is 22 mmHg.

At block 104, a number of formulations for computing a metric of a heart failure variable are stored in memory. Once ePAD, or any other heart failure variable, is measured from a sensed signal for a single cardiac cycle or group of cardiac cycles, a variety of formulations may be conceived for computing a metric for comparison to the stored target value to aid the clinician in recognizing when medical intervention is warranted. The metric formulations will generally include metrics computed over different time intervals to gain different temporal resolution of the monitored variable. For example, formulations may be stored for computing an hourly average ePAD, a daily average ePAD and a weekly average ePAD, which may be a moving average. Formulations may further include computing exponentially-weighted averages. One formula for computing an exponentially weighted moving weekly average (EWMA) is:

$$EWMA(i)=\lambda*P(i)+(1-\lambda)*EWMA(i-1)$$

wherein P(i) is the currently derived ePAD value, EWMA (i−1) is a previously determined EWMA and $0<\lambda<1$.

Figure 4:
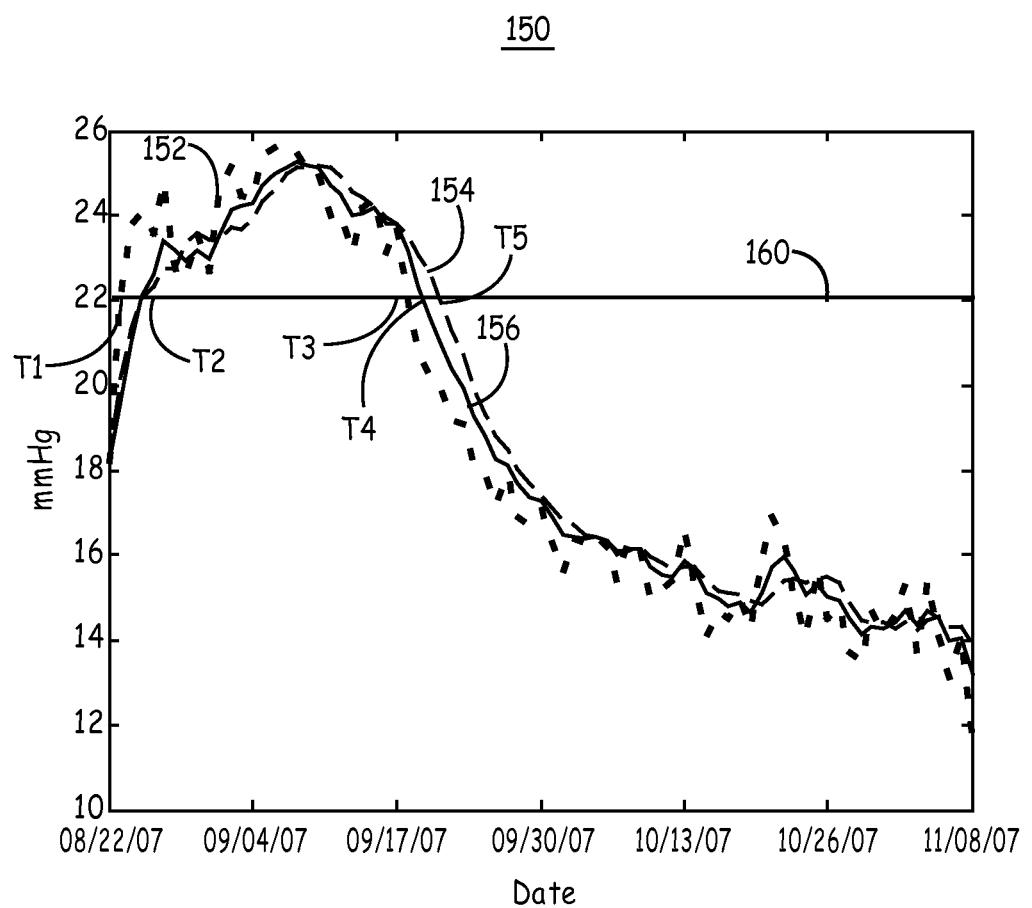
FIG. 4 is a graph of estimated pulmonary artery pressure comparison metrics computed using three different formulations plotted over time.

FIG. 4 is a graph 150 of ePAD comparison metrics computed using three different formulations plotted over time. A daily average ePAD 152 is shown in dotted line. The daily average ePAD may be computed as the average of all ePAD values instantaneously measured from an RV pressure signal over a 24-hour period. A weekly moving average ePAD 154 is shown in dashed line. The moving average may be computed using each instantaneous ePAD measurement or using hourly or daily averages. Alternatively, a non-moving weekly average could be determined after a 7-day period of time. An EWMA ePAD 156 is shown in solid line. The EWMA 156 is computed in this example using the above equation with $\lambda=0.35$.

As can be seen in FIG. 4, each of these comparison metrics cross an ePAD target value 160 at different times. The daily average ePAD 152 exceeds the target value 160 earliest at T1 and falls below the target value earliest at T3. The weekly average 154 and the EWMA 156 exceed the target value at about the same time T2, but the EWMA 156 falls below the target value earlier at T4 than the weekly average at T5. These differences relative to a selected target value may have impact on decisions made by a clinician in managing the heart failure patient. For example, the earliest possible detection may be desired to allow for early intervention. Accordingly, a daily average ePAD may be used as a comparison metric. In other patients, a clinician may prefer to ensure that the ePAD is persistently above the target value before altering medications or taking other interventions and may thus prefer to utilize a weekly average as a comparison metric. Earlier detection of the comparison metric returning to a level at or below the target value may be desirable to allow early adjustment or termination of an intervention so as not to create an exacerbated response in the reverse direction. The desired comparison metric used as a guide for starting, stopping or adjusting clinical, therapeutic interventions may depend on the type of interventions being employed, clinician preference, and individual patient condition.

The target value 160 is shown set at 22 mmHg and is applied to all three comparison metrics 152, 154 and 156. The target value 160 is set for all comparison metrics computed for a given heart failure variable, such as ePAD in this example. The target value is set to a value that is found to be clinically significant in a patient population or in an individual patient. This clinical significance may be based on hospitalizations, morbidity, mortality, patient symptoms, or other monitored parameters or study endpoints. As such, while the target value 160 may be different between patients and may even be adjusted within a patient, it is the intention of one embodiment that the same target value 160 will be always be applied to any and all comparison metrics computed for a given heart failure variable.

Depending on the heart failure variable and comparison metric being used, a target value crossing warranting a notification may be an increasing, positive-going crossing or a decreasing, negative-going crossing. In other words, a target value may be set as a maximum clinically acceptable value or a minimally acceptable value of a heart failure variable. As such, embodiments may include generating a notification when a comparison metric exceeds or falls below a target value.

Referring again to FIG. 3, at block 106, a comparison metric is selected for use in managing the patient. A comparison metric is one of the heart failure variable metrics for which a formulation has been stored, which will be used for comparing to the stored target value. One or more comparison metrics may be selected such that if any one of the selected comparison metrics exceeds the target value, a notification is generated to enable a clinician to prescribe a therapeutic intervention. The clinician may select a single one of the stored metric formulations to compute a single comparison metric preferred for a given patient.

At block 108, the physiological signal(s) required to compute the selected comparison metric(s) are sensed. For example, an RV pressure signal may be sensed for measuring instantaneous ePAD values for computing ePAD comparison metrics. As will be described herein, the comparison metrics may be computed separately for different heart rate ranges, activity levels, respiration rates, postures, or other secondary factors that may be influencing instantaneous ePAD measurements. As such, an activity signal, EGM signal or other secondary signals may also be sensed at block 108 in addition to the primary signal from which the heart failure variable is measured.

If an intervention started flag is not set, as determined at block 110, the selected comparison metric is computed at block 112 using the appropriate formulation stored at block 104. The comparison metric is compared to the target value at block 114. The target value, as discussed previously, is a clinically relevant value of a heart failure variable that, when exceeded, indicates a worsening or progression of the heart failure. The target value may be stored at block 114 as a magnitude only or as a magnitude and a time duration. For example, the target value may be set to 22 mmHg for a minimum of one week for any comparison metric relating to heart failure. As such, if a daily average is computed as a comparison metric, the daily average would be required to exceed 22 mmHg for at least one week before a notification is generated. In another example, a weekly moving average used as a comparison metric might be required to exceed a stored magnitude, such as 22 mmHg, for a stored time duration, such as five days, before the metric would be determined to exceed the target value. A target value time duration could be selected as minutes, hours, days, weeks, etc. By including a time duration as a component of the target value, the likelihood of taking unnecessary medical interventions in response to transient fluctuations in the comparison metric is reduced. The time duration component of a target value may not be needed when the comparison metrics are computed using variable values acquired over relatively long periods of time.

If the comparison metric exceeds the target value, a notification, also referred to herein simply as a "notice", is generated at block 115. The notification is intended to make the clinician aware that the heart failure variable has exceeded the target value and medical intervention may be warranted. The notice generated may include data supporting the notification, such as the selected comparison metric value, the target value, other heart failure variable metrics that may have been computed but not compared to the target value, the last occurrence of the target value being exceeded, and the last occurrence of an intervention notice. Additional patient management information stored by the IMD system, either in the IMD, in an external device 26 (FIG. 1) such as a home monitor, or in the remote patient management database 24 (FIG. 1), may also be included in the notification. Such additional information may include what intervention(s) have been taken previously in response to prior intervention notices, how long the comparison metric remained above the target value following prior intervention notices, the time between when the last intervention was stopped and the current intervention notice, or the like. Such information may be useful to the clinician in prescribing a new intervention and managing the patient going forward.

The notice may be a message transmitted to an external device from the IMD. As such, the notice may be displayed on an external monitor, external programmer, transmitted to a remote patient management database for display to a clinician or transmitted to another communication device, such as a networked computer, cellular telephone, palm-held device or the like. The notice may be generated for transmission to a patient's home monitor for display to a patient so that the patient can seek medical attention. As described above, the notice may be initiated by the IMD but the notice may include data and information gathered from an external device such as a home monitor as well as data stored in a remote patient management database. As such, the action of generating an intervention notice at block 115 may be implemented across IMD system components.

After generating the intervention notice, the IMD may receive a communication indicating that an intervention has been started at block 116. For example, a clinician, using an external programming device or by making an entry in the remote patient management database, may cause a data message to be transmitted back to the IMD indicating an intervention has been initiated. Alternatively, a patient using a home monitor or handheld device may enter input indicating an intervention has started. The IMD sets an "intervention started" flag at block 117.

With the intervention started flag now set, method 100 advances to block 118 where updated metric values are computed and reported at block 120. As long as the intervention flag is set, the comparison metric, and optionally other heart failure variable metrics, may be updated and reported each time they are computed, or at another predetermined time interval. Updated values (or the raw data needed to compute updated metrics) are transmitted from the IMD to an external device. Other data such as patient weight, externally monitored blood pressure data, and patient symptoms may also be updated and transmitted from an external device to a remote patient management database.

In alternative embodiments, reporting updated metrics does not require receiving an intervention started message and setting an intervention started flag. Selected comparison metrics and other heart failure variable metrics may be updated and reported by transmitting data from the IMD to an external device after a notification has been generated and for as long as the selected comparison metric remains greater than the target value or for another predetermined interval of time. In still other embodiments, updated metrics may not be reported until the selected comparison metric is found to be less than the target value.

Once the comparison metric has fallen below the target value, as determined at block 122, a notice is generated at block 124 indicating the heart failure variable has been restored to a stable range, below the target value. The notice may include the comparison metric value and the corresponding time point at which it was found to fall below the target value. The notice may indicate the intervention has been effective and may include episode summary data such as indicating the total time the comparison metric remained above the target value. Method 100 may then return to block 112 to continue monitoring the selected comparison metric(s) relative to the target value.

If an intervention started flag has been set previously at block 117, the IMD may be configured to cancel or reset the flag upon receiving a communication from an external device indicating the intervention has been stopped. As such, at block 126, an external programmer or home monitor may transmit an intervention stopped message to the IMD to cause the IMD to reset or cancel the intervention started flag. In one embodiment, the IMD continues to compute and report updated comparison metrics at block 118 and 120 until the intervention started flag is cancelled. It is recognized that the intervention started flag may be cancelled by a clinician after the heart failure variable has been determined to be stabilized. The intervention itself, for example a new prescribed medication or dosage, may be maintained, adjusted or stopped after stabilization of the heart failure variable as determined by a clinician based on the updated metrics reported at block 120.

After canceling the intervention started flag, updated metrics are no longer reported. Method 100 returns to block 112 to continue monitoring the selected comparison metric(s) relative to the target value.

During operation of method 100, different comparison metrics may be selected for monitoring relative to the target value during different portions of the algorithm. For example, one or more metrics may be initially selected for comparison to the target value at block 114. If only one metric is selected, an intervention notice is generated at block 115 only in response to that one selected metric exceeding the target value. If multiple metrics are selected, any one of the selected comparison metrics exceeding the target value at block 114 would trigger an intervention notice.

Once the notice has been generated, a different metric or set of metrics may be updated and reported at block 118 than the comparison metrics computed at block 112. For example, one selected metric may be used to detect when the metric exceeds the target value at block 114. All of the available formulations may then be used to compute all of the available heart failure variable metrics for updating at block 118 and reporting at block 120. Alternatively, a single metric different than the selected comparison metric used at block 114 may be updated and reported at blocks 118 and 120. For example, a moving weekly average may be selected for comparison to the target value at block 114, and a daily average may be updated and reported at blocks 118 and 120 after the intervention notice has been generated.

Any one of the metrics computed at block 118 falling below the target value at block 122 may cause a notice to be generated at block 124 indicating the heart failure variable has been restored to a stable value below the target value. In some embodiments, a selected one of the comparison metrics, which may be the same or different than the comparison metric selected for comparison to the target value at block 114, may be used for detecting when the target value has been crossed again.

In summary, the comparison metric(s) used to detect the onset of an unstable heart failure variable (block 114), the comparison metric(s) updated and reported after detecting the onset of the unstable heart failure variable (blocks 118 and 120), and the comparison metrics(s) used to detect when the heart failure variable has again been stabilized below the target value (block 122) may each be distinct from each other. An "unstable heart failure variable" refers generally to a heart failure variable for which a computed comparison metric exceeds a patient management target value, indicating heart failure instability. As such, an "unstable" variable does not necessarily refer to the variability of the value or how quickly it is changing but merely whether a comparison metric computed for the variable is greater than or less than the target value. In the example used herein, the heart failure variable of ePAD is used with a defined target value, for example 22 mmHg, such that when a comparison metric is computed for ePAD is greater than 22 mmHg the ePAD is considered to be unstable, i.e., indicating a worsening progression of heart failure.

It is recognized that, depending on the heart failure variable and metric formulations being used, a comparison metric less than a target value magnitude, rather than greater than, would indicate an unstable heart failure variable. Furthermore, it is recognized that for any given heart failure variable both an upper bound target value and a lower bound target value may be stored. The upper bound and lower bound would define a clinically acceptable range of the heart failure variable. This range may be a default range determined for a patient population or a patient-specific range based on data acquired from an individual patient. For example, an upper bound for ePAD may be 22 mmHg and a lower bound may be 10 mmHg. Whenever an ePAD comparison metric exceeds the upper bound or falls below the lower bound (for a target value time duration if required), a notification would be generated.

Figure 5:
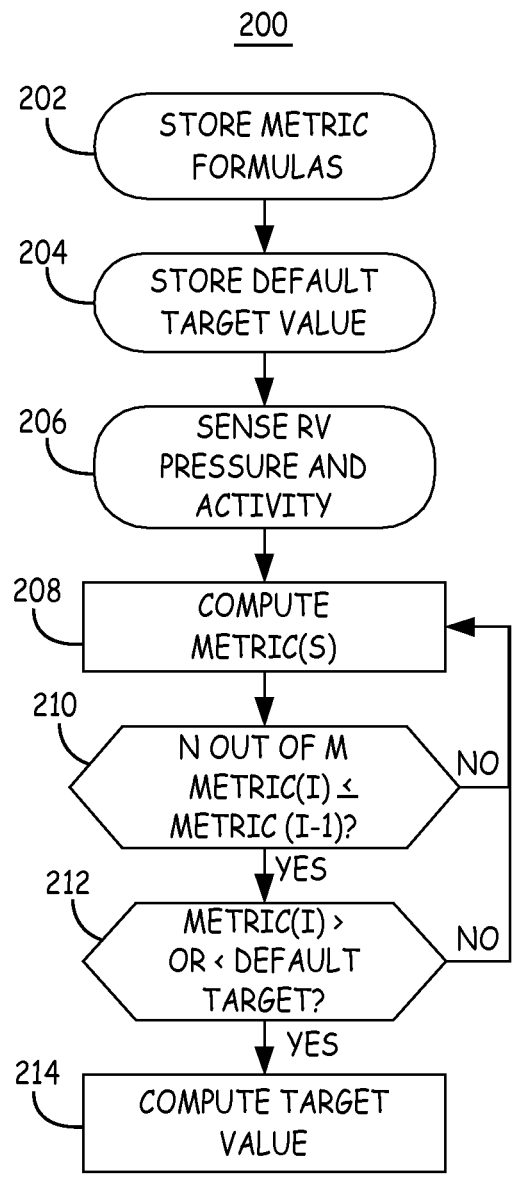
FIG. 5 is a flow chart of one method for computing a target value of a heart failure variable used in patient management.

FIG. 5 is a flow chart of one method for computing a target value of a heart failure variable used in patient management. Selection and setting of the target value may be done manually, after observation by the clinician, or automatically, after a prescribed time period, by the IMD. Method 200 represents an automatic method for adjusting a target value in an individual patient. Method 200 may be performed after initial implant of the IMD for determining an appropriate target value for an individual patient. Typically, method 200 will be initiated after a post-operative recovery period, for example after one to two weeks following surgery. Method 200 may then be performed over a predetermined time period, e.g., a desired number of days or weeks, for acquiring data used to compute an individualized target value.

At block 202, the formulas for computing heart failure variable metrics are stored in memory. At block 204, a default target value is stored. The default target value may be a target value determined from a patient population or may be selected by a clinician for an individual patient. This default value will be the lowest target value utilized by an algorithm monitoring a selected comparison metric. In one embodiment, the default target value is set at a population mean plus one standard deviation At block 206, primary and secondary physiological signals are sensed, which are needed for computing the heart failure variable metrics at block 208. In one embodiment, ePAD metrics used to determine an individualized target value are computed using an RV pressure signal and an activity signal. Separate ePAD metrics are computed for low activity and for high activity. As such, the activity signal is needed to properly store and utilize ePAD values acquired during low activity, e.g. an activity count less than a predetermined activity threshold, and/or ePAD values acquired during high activity, i.e. an activity count greater than the predetermined activity threshold.

If a metric used to compute a target value is a daily average, all of the ePAD values obtained when the activity count was below the threshold are averaged to obtain a "resting" daily average ePAD metric. All of the ePAD values obtained when the activity count was above the activity threshold may also be averaged to obtain an "active" daily average ePAD metric. In alternative embodiments, time of day, heart rate, posture, temperature, or respiration rate might be used to compute separate ePAD metrics for night and day, low and high heart rate, upright and non-upright positions, low and high core body temperatures, and low and high respiration rates, respectively. Daily average metrics, or the raw data, may additionally be used to compute other metrics such as a weekly moving average and an exponentially-weighted moving weekly average.

One or more different metrics may be computed at block 208. At block 210, a newly computed comparison metric, metric(i) is compared to the previously computed metric, metric(i−1), to determine if the metric is exhibiting an increasing trend. If a selected number N out of the most recent M computed metrics are less than or equal to the previously computed metric the metric does not exhibit an increasing trend. If the metric is not increasing and is different than the stored default target value, as determined at block 212, the newly computed metric is used in computing a new target value at block 214. In one embodiment, a daily average ePAD is used to compute the target value.

The metric(i) may be greater than or less than the default target value, as determined at block 212, indicating that the target value for the individual patient should be adjusted from a population mean or other generally determined default target value. This adjustment may be to lower the target value or to increase the target value as appropriate for the patient based on initial baseline monitoring of the comparison metric.

An adjustment to the target value may include an adjustment of the required magnitude component and/or a required time duration component of the target value. As described previously, the target value may include a required time duration that a comparison metric must exceed a target value magnitude before generating a notification. This target value time duration component may be adjusted at block 212 based on a patient's specific baseline data.

To illustrate, suppose a default target value for ePAD comparison metrics is set at block 204 to a magnitude of 22 mmHg required for a time duration of five days. A patient may have a relatively high baseline daily average ePAD, e.g., near or even greater than the default 22 mmHg. In this case the target value magnitude component may be increased at block 214 to a higher magnitude, e.g., 26 mmHg. Additionally or alternatively, the target value time duration component may be shortened at block 214, e.g., two days instead of five days. A patient with a relatively higher baseline daily average ePAD may be less tolerant of further increases in pressure than patients having a lower daily average ePAD. An earlier notification, therefore, may be desired in patient's experiencing higher baseline ePAD measurements. This can be accomplished by shortening the required time duration component of the target value.

A target value may be stored separately for different levels or ranges of secondary variables, e.g., for both the high and low activity levels, heart rate, respiration rate, posture, body temperature, or time of day. During ambulatory monitoring of the comparison metrics, as described in conjunction with FIG. 3, the selected comparison metric(s) will be computed separately for the same secondary variables used in computing the target values. The comparison metrics will then be compared to the appropriate target value as they are determined.

Referring again to block 210, if the metric exhibits an increasing trend or is less than the default target value, the metric is not used to compute a new target value. Method 200 returns to block 208 to continue computing new values of the comparison metric(s).

One or more values computed for a given metric may be used in computing the target value. In one embodiment, the target value may be set equal to a single computed metric, an average of a predetermined number of computed metrics or other function of a comparison metric, such as a daily average. In other embodiments, differently computed metrics may be used in computing the target value, such as both a daily average and a weekly moving average.

The method 200 may be performed during an initial "learning" period to set the target value for an individual patient based on measurements performed within that patient. Once the target value is computed and stored, that target value is used regardless of which metric is selected as a comparison metric for monitoring a given heart failure variable relative to the target value. In alternative embodiments, method 200 may be performed on a continuous or periodic basis for updating the target value for a given heart failure variable over time.

Thus, apparatus and associated methods for use in managing patients have been presented in the foregoing description with reference to specific embodiments. It is appreciated that various modifications to the referenced embodiments may be made without departing from the scope of the invention as set forth in the following claims.

The invention claimed is:

1. An implantable medical device, comprising;
   a physiological sensor;
   a memory storing a target value for a physiological variable and storing a plurality of formulations for computing a plurality of averaged metrics of the physiological variable;
   a control unit configured for selecting a formulation for computing a first averaged metric of the plurality of averaged metrics and a second averaged metric of the plurality of averaged metrics from the plurality of formulations for computing a plurality of averaged metrics of the physiological variable, receiving a signal from the physiological sensor, computing the first averaged metric of the variable using the signal extending over a first periodic time interval and the second averaged metric of the variable using the signal extending over a second periodic time interval longer than and including the first periodic time interval such that the first and second averaged metrics provide different temporal resolutions of the physiological variable, and separately comparing each of the first averaged metric and the second averaged metric to the stored target value; and
   a notification module configured for generating a notice in response to the comparisons of the computed metrics to the target value, wherein the memory stores the identity of the selected first averaged metric and the second averaged metric, and the notification module generates the notice in response to both the selected formulation and the comparison of the selected first averaged metric and the second averaged metric and the target value.

2. The device of claim 1 wherein each of the plurality of formulations correspond to a time interval for computing the metric, wherein at least one formulation corresponds to a first time interval and another formulation corresponds to a second time interval greater than the first time interval.

3. The device of claim 1 wherein the control unit computes updated values of one of the plurality of metrics, and
   the notification module generates reports of the computed updated metric values at predetermined time intervals after generating the notice.

4. The device of claim 1 wherein the notice comprises a time interval since a previous notice.

5. The device of claim 3 wherein the notification module receives an intervention initiated message, and
   the control unit sets an intervention started flag in response to the received message.

6. The device of claim 5 wherein the notification module receives an intervention stopped message and generates reports of the updated metric values at predetermined time intervals until the intervention stopped notice is received.

7. The device of claim 1 wherein the physiological sensor is a pressure sensor.

8. The device of claim 2 wherein the physiological variable is an estimated pulmonary artery diastolic pressure (ePAD).

9. The device of claim 8 wherein the plurality of formulations comprise a daily average ePAD, a weekly average ePAD, and an exponentially weighted weekly average ePAD.

10. The device of claim 8 wherein the target value is 22 mmHg.

11. The device of claim 1 wherein the target value comprises a magnitude and a time duration.

12. The device of claim 1 further comprising a second sensor sensing a signal for measuring a secondary variable having a secondary affect on the physiological variable, wherein the plurality of formulations comprise a first formulation for computing the selected metric at a first level of the secondary variable and a second formulation for computing the selected metric at a second level greater than the first level of the secondary variable.

13. The device of claim 12 wherein the secondary variable is one of heart rate, activity, respiration rate, posture, and time of day.

14. The device of claim 1 wherein the control unit determines the target value in response to the sensed physiological signal.

15. A method for use in an implantable medical device system, comprising;
   storing a target value for a physiological variable;
   storing a plurality of formulations for computing a plurality of averaged metrics of the physiological variable;
   selecting a formulation for computing a first averaged metric of the plurality of averaged metrics and a second averaged metric of the plurality of averaged metrics from the plurality of formulations for computing a plurality of averaged metrics of the physiological variable;
   sensing a physiological signal;
   computing the first averaged metric of the variable using the signal extending over a first periodic time interval and the second averaged metric of the variable using the signal extending over a second periodic time interval longer than and including the first periodic time interval such that the first and second averaged metrics provide different temporal resolutions of the physiological variable;

separately comparing each of the first averaged metric and the second averaged metric to the stored target value; and generating a notice in response to the comparisons of the computed metrics to the target value, wherein the notice is generated in response to both the selected formulation and the comparison of the selected first averaged metric and the second averaged metric and the target value.

16. The method of claim 15 wherein each of the plurality of formulations correspond to a time interval for computing the metric, wherein at least one formulation corresponds to a first time interval and another formulation corresponds to a second time interval greater than the first time interval.

17. The method of claim 15 further comprising computing updated values of one of the plurality of metrics; and generating a report of the computed updated metric values at predetermined time intervals after generating the notice.

18. The method of claim 15 wherein the notice comprises a time interval since a previous notice.

19. The method of claim 17 further comprising receiving an intervention initiated message, and setting an intervention started flag in response to the received message.

20. The method of claim 19 further comprising:

receiving an intervention stopped message; and generating the report at predetermined time intervals until the intervention stopped notice is received.

21. The method of claim 15 wherein the physiological signal is a pressure sensor.

22. The method of claim 21 wherein the physiological variable is an estimated pulmonary artery diastolic pressure (ePAD).

23. The method of claim 22 wherein the plurality of formulations comprise a daily average ePAD, a weekly average ePAD, and an exponentially weighted weekly average ePAD.

24. The method of claim 22 wherein the target value is 22 mmHg.

25. The method of claim 15 wherein the target value comprises a magnitude and a time duration.

26. The method of claim 15 further comprising:

sensing a signal for measuring a secondary variable having a secondary affect on the physiological variable, wherein the plurality of formulations comprise a first formulation for computing the selected metric at a first level of the secondary variable and a second formulation for computing the selected metric at a second level greater than the first level of the secondary variable.

27. The method of claim 26 wherein the secondary variable is one of heart rate, activity, respiration rate, posture, and time of day.

28. The method of claim 15 further comprising determining the target value in response to the sensed physiological signal.

29. A non-transitory computer readable medium for storing a set of instructions which when implemented in an implantable medical device system cause the system to:

store a target value for a physiological variable;

store a plurality of formulations for computing a plurality of averaged metrics of the physiological variable;

selecting a formulation for computing a first averaged metric of the plurality of averaged metrics and a second averaged metric of the plurality of averaged metrics from the plurality of formulations for computing a plurality of averaged metrics of the physiological variable;

sense a physiological signal;

compute the first averaged metric of the variable using the signal extending over a first periodic time interval and the second averaged metric of the variable using the signal extending over a second periodic time interval longer than and including the first periodic time interval such that the first and second averaged metrics provide different temporal resolutions of the physiological variable;

separately compare each of the first averaged metric and the second averaged metric to the stored target value; and generate a notice in response to the comparisons of the computed metrics to the target value, wherein the notice is generated in response to both the selected formulation and the comparison of the selected first averaged metric and the second averaged metric and the target value.

* * * * *